(12) United States Patent
Stonecipher

(10) Patent No.: US 10,189,335 B2
(45) Date of Patent: Jan. 29, 2019

(54) FILTER

(71) Applicant: Caterpillar Inc., Peoria, IL (US)

(72) Inventor: Kenneth Stonecipher, Metamora, IL (US)

(73) Assignee: Caterpillar Inc., Deerfield, IL (US)

( * ) Notice: Subject to any disclaimer, the term of this patent is extended or adjusted under 35 U.S.C. 154(b) by 349 days.

(21) Appl. No.: 14/872,631

(22) Filed: Oct. 1, 2015

(65) Prior Publication Data

US 2017/0095760 A1   Apr. 6, 2017

(51) Int. Cl.
*B60H 3/06* (2006.01)
*B01D 39/16* (2006.01)
(Continued)

(52) U.S. Cl.
CPC ....... *B60H 3/0608* (2013.01); *B01D 39/1615* (2013.01); *C12N 1/14* (2013.01); *C12N 11/12* (2013.01); *C12N 13/00* (2013.01); *B01D 2239/0407* (2013.01); *B01D 2239/0478* (2013.01); *B01D 2239/0492* (2013.01); *B01D 2239/065* (2013.01); *B01D 2239/1208* (2013.01)

(58) Field of Classification Search
CPC .............. B01D 39/18; B01D 39/1692; B01D 2239/10; B01D 2239/65; B01D 2239/266; B01D 2239/407; B01D 2239/478; B01D 2239/492; B01D 2239/0407; B01D 2239/0478; B01D 2239/065; B01D 2239/1208; B01D 39/1615; B60H 3/608; B60H 3/0608; C12N 1/14; C12N 11/12; C12B 13/00

See application file for complete search history.

(56) References Cited

U.S. PATENT DOCUMENTS 8,298,809 B2   10/2012   Kalisz et al.
2007/0160766 A1*   7/2007   Copeland .................. C09D 5/14
                                                              427/407.1
(Continued)

FOREIGN PATENT DOCUMENTS

GB   2188135   11/1989
GB   2199315   7/1991
(Continued)

*Primary Examiner* — Robert Clemente
(74) *Attorney, Agent, or Firm* — Miller, Matthias & Hull

(57) ABSTRACT

A filtration material is disclosed that may include a first layer comprising a first three-dimensional network of fibers including a first plurality of cells, including an extracellular matrix comprising α-glucan and chitin. The filtration material may include a second layer fluidly downstream of the first layer comprising a second three-dimensional network of fibers including a second plurality of cells, including an extracellular matrix including α-glucan and chitin and the second layer may be adhered to the first layer. The first layer and the second layer may be coated with a polymer mixture including a polymer configured to mitigate exposure of the first and second three-dimensional network of fibers to glucanases and chitanases and further resist thermal degradation below a predetermined temperature. The polymer mixture may further include an antioxidant at an amount sufficient to mitigate the polymer from thermally degrading below the predetermined temperature.

18 Claims, 7 Drawing Sheets

(51) Int. Cl.
*C12N 13/00* (2006.01)
*C12N 1/14* (2006.01)
*C12N 11/12* (2006.01)

(56) References Cited

U.S. PATENT DOCUMENTS

| | | |
|---|---|---|
| 2008/0120954 A1 | 5/2008 | Duello et al. |
| 2012/0000847 A1 | 1/2012 | Losma |
| 2014/0013941 A1 | 1/2014 | Stinzendoerfer et al. |
| 2015/0273407 A1* | 10/2015 | Gil .................. C07K 14/37 |
| | | 210/650 |

FOREIGN PATENT DOCUMENTS

| | | |
|---|---|---|
| JP | S62129633 | 6/1987 |
| JP | 4851739 | 1/2012 |
| WO | 2014164127 | 10/2014 |

* cited by examiner

FILTER

TECHNICAL FIELD

This disclosure generally relates to filters and, more specifically, relates to degradable filters.

BACKGROUND

An air supply system associated with a vehicle cabin may include a filtration system. The filtration system may include a contaminated air stream conduit fluidly connecting an air contaminated air stream to a filter assembly, and a filtrate stream conduit fluidly connecting a purified air stream to the vehicle cabin. The filter assembly may be configured to preclude passage of solid, gaseous and aerosol contaminants of the contaminated air stream, and in doing so, provide the purified air stream to the vehicle cabin.

One cabin filter assembly design is described by US 2014/0013941 to Stinzendoerfer et al. (the '941 publication). As seen there, the '941 publication describes a cabin filter assembly including a combination of a cellulosic and synthetic foam filtration material impregnated with activated carbon or an ion-exchange resin. The cellulosic and synthetic foam filtration materials may be used to filter solid particulates, while the activated carbon or ion-exchange resin may be used to remove gaseous contaminants. Further, the '941 publication describes a sealing element disposed around the circumference of the filtration materials comprising a polyurethane foam.

Importantly, the '941 publication describes its filter assembly including cellulosic materials and synthetic foams, such as polyurethane foams. After use, the '941 publication filter assembly may be placed in a landfill where it takes up considerable volume. Further, due to its use of cellulosic and synthetic foams, the volume occupied by this filter assembly will not diminish for years. Accordingly, a need exists to provide a cabin air filter assembly that precludes solid, gaseous and aerosol contaminants of the air contaminated air stream from passing through its filtration material, while utilizing materials that more easily degrade when the filter assembly is placed in a landfill.

The present disclosure is directed to overcoming one or more problems set forth above and/or other problems associated with the prior art.

SUMMARY

In accordance with one aspect of the present disclosure, a filtration material is disclosed. The filtration material may include a first layer comprising a first three-dimensional network of fibers including a first plurality of cells, the first plurality of cells may include an extracellular matrix comprising α-glucan and chitin and the first layer may be configured to preclude passage of solid materials of a contaminated air stream. The filtration mater may further include a second layer fluidly downstream of the first layer comprising a second three-dimensional network of fibers including a second plurality of cells, the second plurality of cells may include an extracellular matrix including α-glucan and chitin and the second layer may be configured to preclude passage of solid materials of the contaminated air stream, the second layer being adhered to the first layer. The first layer and the second layer may be coated with a polymer mixture, the polymer mixture including a polymer and an antioxidant, the polymer configured to mitigate exposure of the first three-dimensional network of fibers and the second three-dimensional network of fibers to glucanases and chitanases, the polymer further configured to begin thermally degrading at or above a predetermined temperature, the antioxidant being included at an amount sufficient to mitigate the polymer from thermally degrading below the predetermined temperature.

In accordance with another aspect of the present disclosure, a filter assembly is disclosed. The filter assembly may include a first layer of filtration material comprising a first perimeter and first three-dimensional network of fibers including a first plurality of cells, the first plurality of cells may include an extracellular matrix comprising α-glucan and chitin, the first layer of filtration material may be configured to preclude passage of solid materials of a contaminated air stream. The filter assembly may further include a second layer of filtration material fluidly downstream of the first layer comprising second perimeter and a second three-dimensional network of fibers including a second plurality of cells, the second plurality of cells may include an extracellular matrix including α-glucan and chitin, the second layer of filtration material may be configured to preclude passage of solid materials of the contaminated air stream, the second layer of filtration material may be adhered to the first layer of filtration material. Additionally, the filter assembly may include a frame surrounding the first perimeter and the second perimeter including a plurality of cellulosic fibers having a length to diameter ratio of at least ten to one, the frame may further include a third three-dimensional network of fibers including a third plurality of cells, the third plurality of cells including an extracellular matrix comprising α-glucan and chitin, the third plurality of cells may envelop the plurality of cellulosic fibers, the frame being configured to retain the first layer of filtration material and the second layer of filtration material, such as by, for example, a compression fit. Lastly, the first three-dimensional network of fibers, the second three-dimensional network of fibers and the third three-dimensional network of fibers may be coated with a polymer mixture, the polymer mixture may include a polymer and an antioxidant, the polymer may be configured to mitigate exposure of the first three-dimensional network of fibers, the second three-dimensional network of fibers and the third three-dimensional network of fibers to glucanases and chitanases and the polymer may be further configured to begin thermally degrading at or above a predetermined temperature, while the antioxidant be included at an amount sufficient to mitigate the polymer from thermally degrading below the predetermined temperature.

In accordance with another embodiment of the present disclosure, a method of manufacturing a filter assembly is disclosed. The method may include, growing mycelium for a period of one to twenty days while exposed to a magnetic field to produce a live first layer of filtration material comprising a first three-dimensional network of fibers and curing the live first layer of filtration material comprising a first three-dimensional network of fibers by at a temperature of at least one hundred and fifty degrees Fahrenheit to terminate growth of the live first layer of filtration material comprising a first three-dimensional network of fibers. The method of manufacturing a filter assembly may further comprise growing mycelium for a period of one to twenty days while exposed to a magnetic field to produce a live second layer of filtration material comprising a second three-dimensional network of fibers and curing the live second layer of filtration material comprising a second three-dimensional network of fibers at a temperature of at least one hundred and fifty degrees Fahrenheit to terminate growth of the live second layer of filtration material comprising a second three-dimensional network of fibers. Lastly, the method of manufacturing a filter assembly may comprise arranging a plurality of cellulosic fibers in one direction and growing mycelium for a period of one to twenty days while exposed to a magnetic field to produce a frame including a live third three-dimensional network of fibers, the live third three-dimensional network of fibers enveloping the plurality of cellulosic fibers and curing the live third three-dimensional network of fibers at a temperature of at least one hundred and fifty degrees Fahrenheit to terminate growth of the live third three-dimensional network of fibers.

These and other aspects and features of the present disclosure will be more readily understood when read in conjunction with the accompanying drawings.

BRIEF DESCRIPTION

Figure 2:
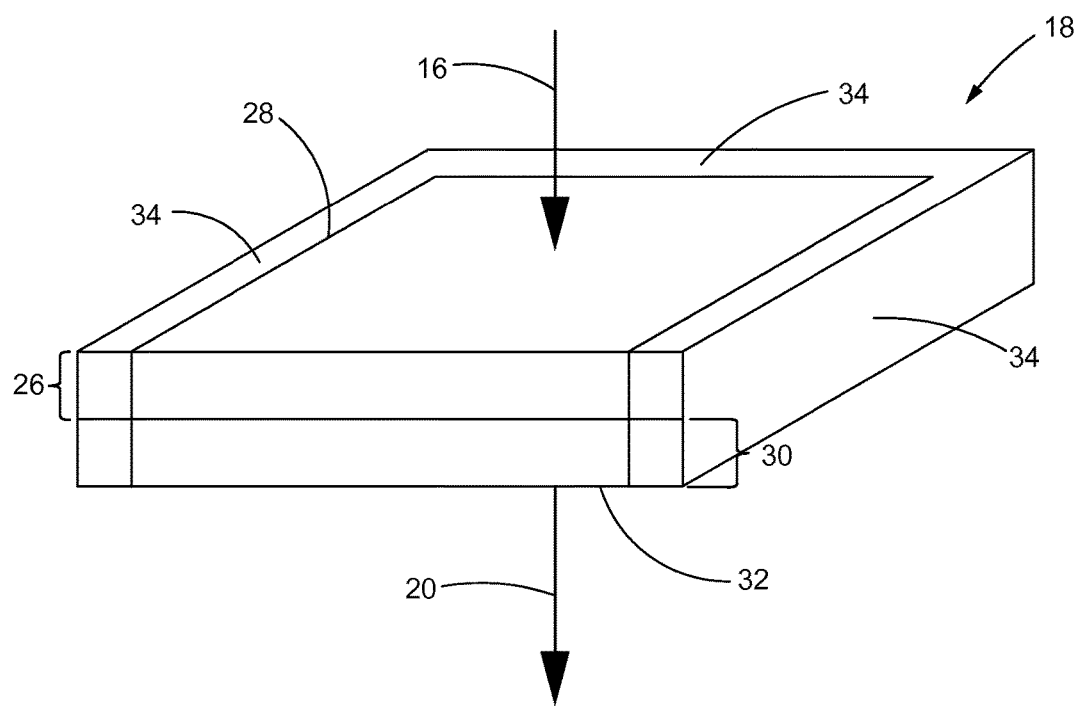
FIG. 2 is a perspective view of an exemplary filter assembly that may be utilized with the air supply system according to FIG. 1 of the present disclosure.
Figure 3:
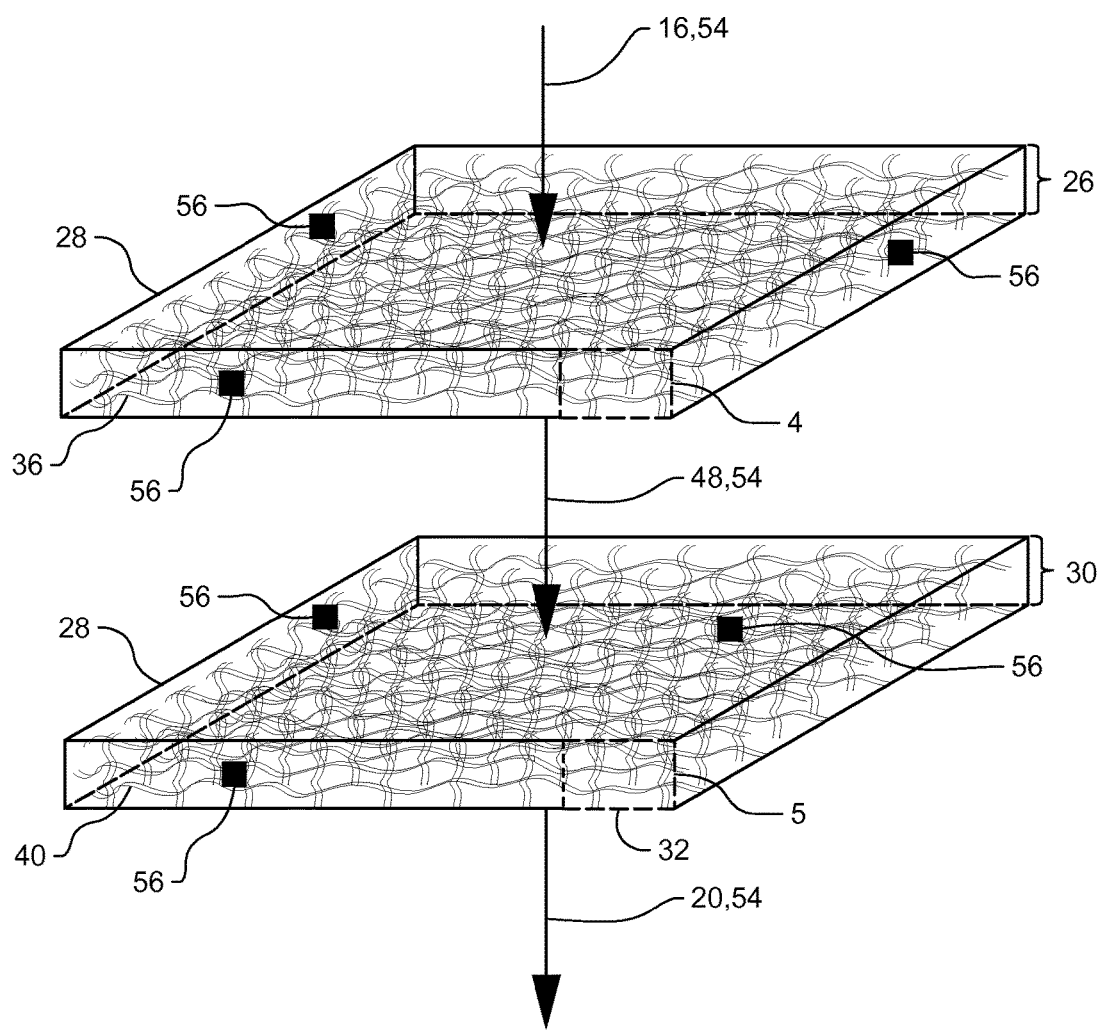
FIG. 3 is an isometric exploded view of an exemplary first layer of filtration material and second layer of filtration material that may be utilized with the filter assembly according to FIG. 2 of the present disclosure.
Figure 8:
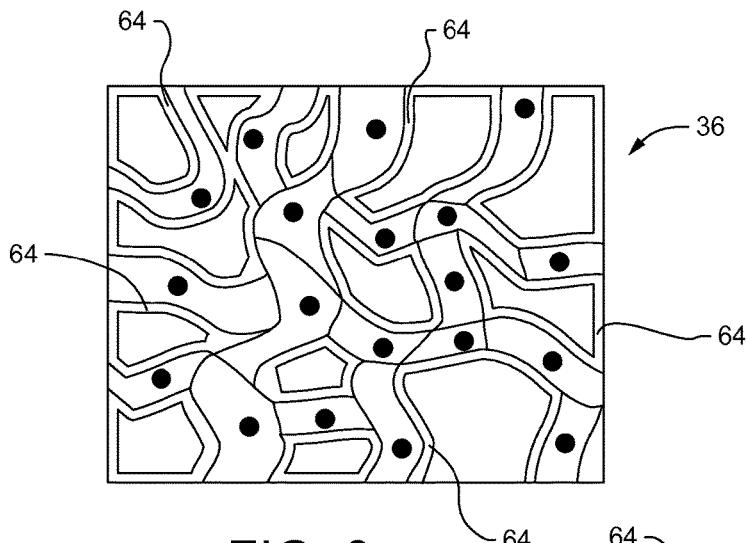

FIG. 8 in an enlarged plan view of portion 4 of FIG. 3 depicting additional features of the exemplary first layer of filtration material that may be utilized with the filter assembly according to FIG. 2 of the present disclosure.

Figure 9:
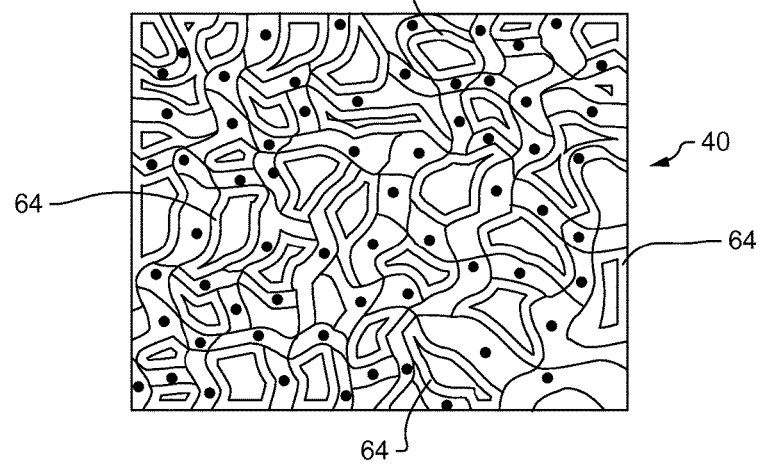

FIG. 9 is an enlarged plan view of portion 5 of FIG. 3 depicting additional features of the exemplary second layer of filtration material that may be utilized with the filter assembly according to FIG. 2 of the present disclosure.

Figure 6:
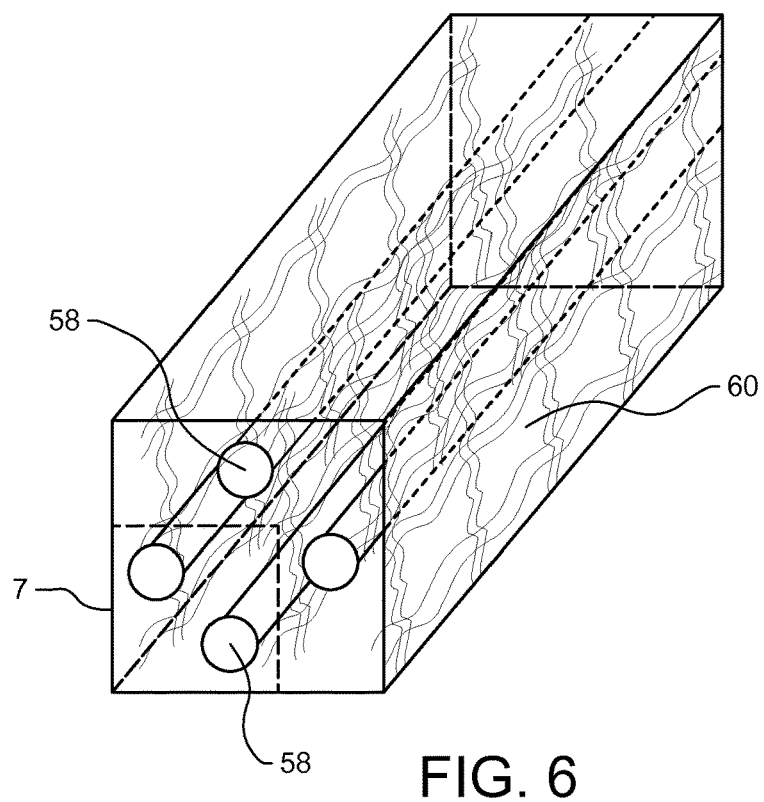
FIG. 6 is an isometric view of an exemplary frame that may be utilized with the filter assembly according to FIG. 2 of the present disclosure.
Figure 10:
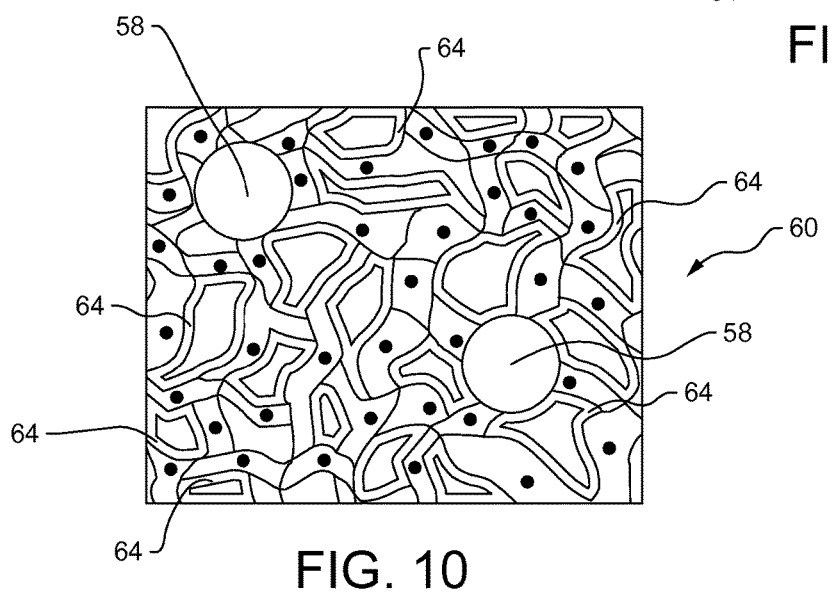

FIG. 10 is an enlarged plan view of portion 7 of FIG. 6 depicting additional features of the exemplary frame that may be utilized with the filter assembly according to FIG. 2 of the present disclosure.

Figure 11:
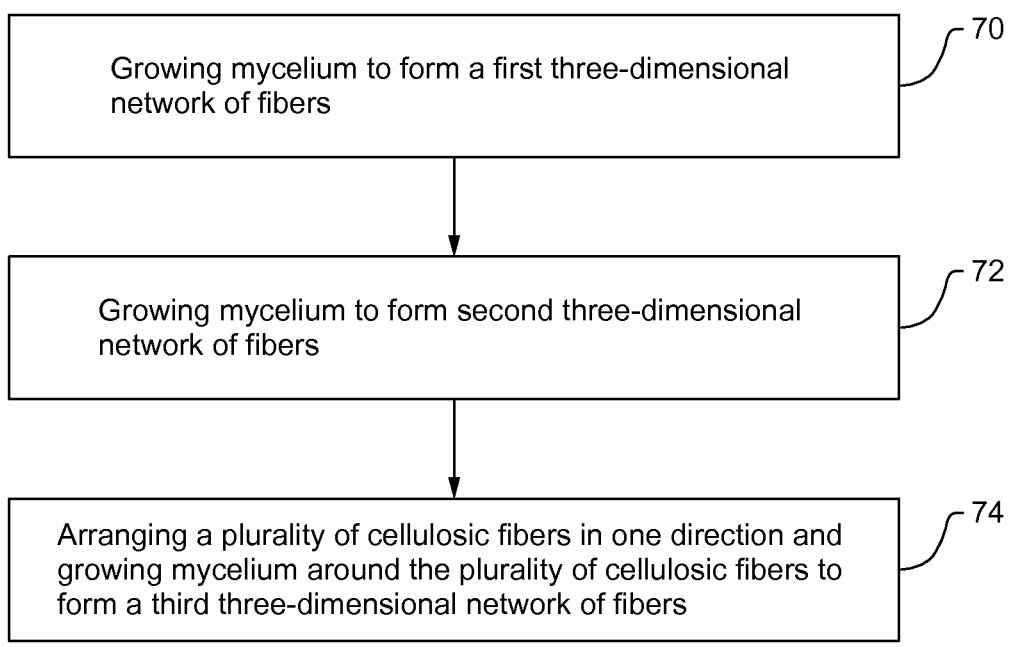

FIG. 11 is a flowchart illustrating exemplary steps of a method for manufacturing a filter assembly according to FIG. 2 of the present disclosure.

DETAILED DESCRIPTION OF THE DISCLOSURE

Figure 1:
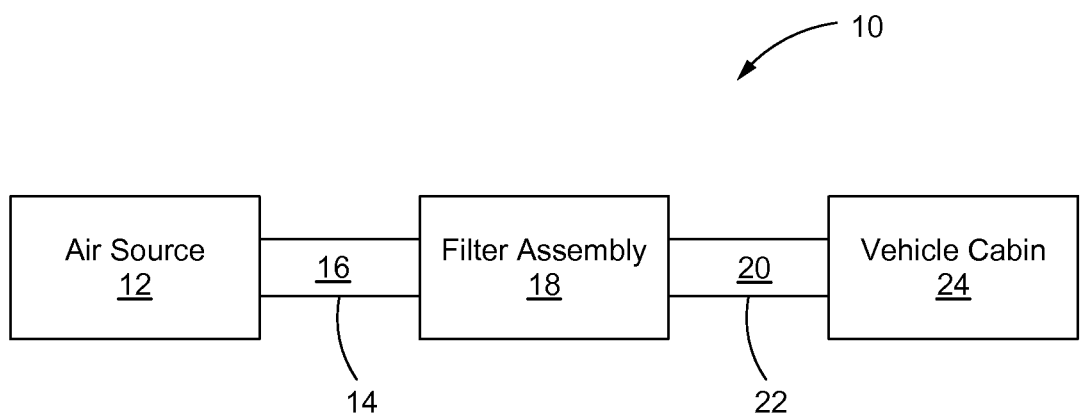
FIG. 1 is a block diagram of an exemplary air supply system for a vehicle cabin according to one aspect of the present disclosure.

Various aspects of the disclosure will now be described with reference to the drawings, wherein like reference numbers refer to like elements, unless specified otherwise. Referring to FIG. 1, a block diagram of an exemplary air supply system 10 is illustrated, according to an aspect of the disclosure. The air supply system 10 may be used to supply air to a vehicle, such as, but not limited to, an automobile, an on-highway truck, an earth moving machine, a track-type tractor, a combine, a tractor, or the like. In one embodiment, the air supply system 10 may be used to provide air to an off-highway truck, such as those used in the mining and quarry industries. However, the air supply system 10 may be associated with any industry including, but not limited to, transportation, construction, forestry, agriculture, material handling and the like. The air supply system 10 may include an air source 12 including solid, gaseous and/or aerosol contaminants. For example, when the air supply system 10 is utilized with an off-highway truck, the air source 12 may include solid contaminants, such as, but not limited to, rock dust or coal dust. Alternatively, when the air supply system 10 is utilized with a tractor, the air source 12 may include gaseous and/or aerosol phase herbicides and/or pesticides such as when the tractor is being utilized to apply herbicides and/or pesticides to a field. Further, when the air supply system 10 is utilized with an automobile or an on-highway truck, the air source 12 may include solids and gaseous and/or aerosol phase carbon monoxide and/or carbon dioxide from other vehicles.

The air supply system 10 of FIG. 1 may further include a contaminated air conduit 14 in fluid communication with the air source 12 configured to convey a contaminated air stream 16 towards a filter assembly 18. The filter assembly 18 may positioned downstream of and be in fluid communication with the contaminated air conduit 14. The filter assembly 18 may be configured to preclude passage of the solid, gaseous and aerosol materials of the contaminated air stream 16 and thereby create a purified air stream 20 devoid of the solid, gaseous and aerosol contaminants of the contaminated air stream 16. The air supply system 10 may further include a purified air stream conduit 22 positioned downstream of an in fluid communication with the filter assembly 18. The purified air stream conduit 22 may be configured to direct the purified air stream 20 away from the filter assembly 18. Lastly, the air supply system 10 may include a vehicle cabin 24. The vehicle cabin 24 may be a space where a vehicle operator is located to control the operation of the automobile, on-highway truck, off-highway truck, earth moving machine, track-type tractor, combine, tractor or the like. The vehicle cabin 24 may be positioned downstream of and be in fluid communication with the purified air stream conduit 22.

While the filter assembly 18 disclosed herein is depicted as being utilized to supply the purified air stream 20 to a vehicle cabin 24, it should be understood that such filter assembly 18 may alternatively be utilized to provide the purified air stream 20 to an internal combustion engine such as a reciprocating piston engine or a gas turbine engine, for example. Further, the filter assembly 18 disclosed herein may find additional use outside of vehicles. For example, the filter assembly 18 may find use with heating, ventilation and air conditioning systems. Therefore, while the illustrations depicted herein disclose the use of the filter assembly 18 with vehicles, this depiction is only exemplary and is not meant to limit its use to vehicle cabins or as a filtration element for internal combustion engines.

Turning to FIG. 2, a perspective view of an exemplary filter assembly 18 that may be utilized with the air supply system 10 of present disclosure is depicted. As seen there, the filter assembly 18 may include a first layer of filtration material 26 having a first perimeter 28 and a second layer of filtration material 30 fluidly downstream of the first layer of filtration material 26 having a second perimeter 32. The first layer of filtration material 26 and the second layer of filtration material 30 may be configured to preclude passage of solid materials of the contaminated air stream 16 and thereby create a purified air stream 20. Further, the second layer of filtration material 30 may be adhered to the first layer of filtration material 26. In addition, the filter assembly 18 may include a frame 34 that surrounds the first perimeter 28 and the second perimeter 32 of the first layer of filtration material 26 and the second layer of filtration material 30, respectively. While FIG. 2 only depicts frame 34 partially surrounding the first perimeter 28 and second perimeter 32, in a preferred embodiment that frame 34 surrounds a complete first perimeter 28 and second perimeter 32, as this particular view is used to illustrate the filter assembly 18 including multiple layers of filtration materials. Further, frame 34 may be configured to retain the first layer of filtration material 26 and the second layer of filtration material 30, and may be additionally configured to form a sealing engagement with a housing that may optionally surround the filter assembly 18 thereby providing a seal between the contaminated air stream 16 and the purified air stream 20 and the filter assembly 18.

Figure 4:
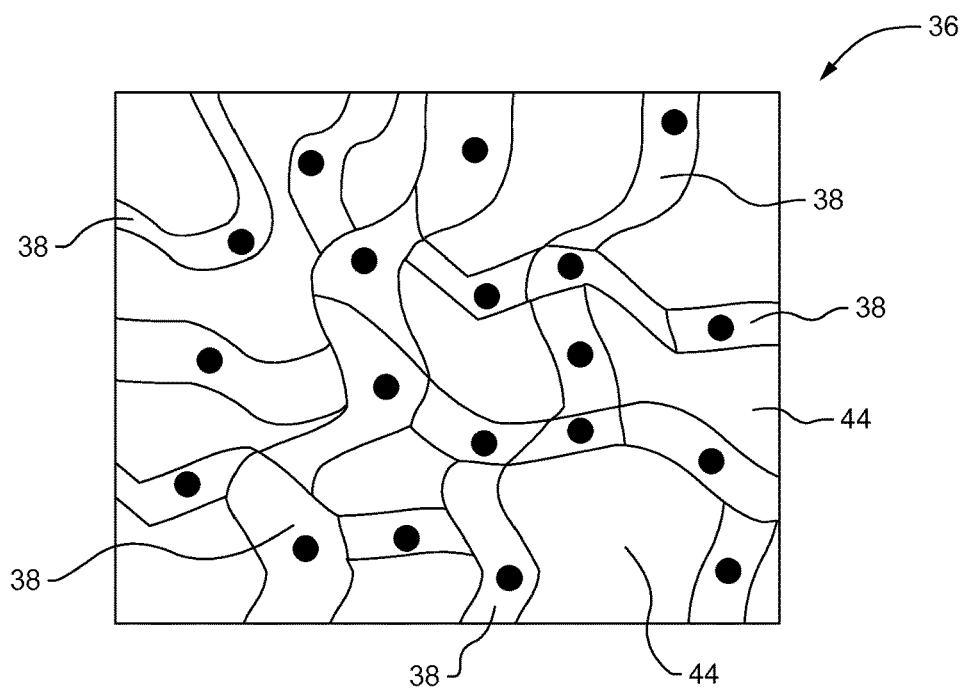
FIG. 4 is an enlarged plan view of portion 4 of FIG. 3.
Figure 5:
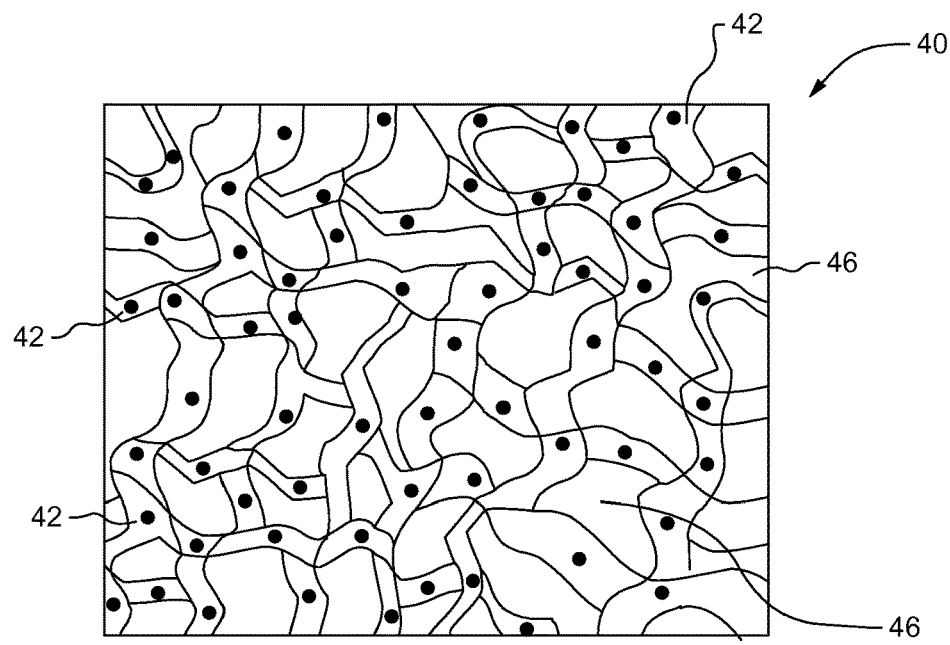
FIG. 5 is an enlarged plan view of portion 5 of FIG. 3.

FIG. 3 depicts an isometric exploded view of an exemplary first layer of filtration material 26 and second layer of filtration material 30 that may be utilized with the filter assembly 18 of the present disclosure. As illustrated there, the first layer of filtration material 26 may include a first three-dimensional network of fibers 36. Turning now to FIG. 4, the first three-dimensional network of fibers 36 may include a first plurality of cells 38, and the first plurality of cells 38 may include an extracellular matrix including α-glucan and chitin. The extracellular matrix of the first plurality of cells 38 may include α-glucan and chitin because the first three-dimensional network of fibers 36 may be a three-dimensional network of mycelium fibers. As further illustrated in FIG. 3, the second layer of filtration material 30 may include a second three-dimensional network of fibers 40. Turning to FIG. 5, the second three-dimensional network of fibers 40 may include a second plurality of cells 42, and the second plurality of cells 42 may include an extracellular matrix including α-glucan and chitin. The extracellular matrix of the second plurality of cells 38 may include α-glucan and chitin because the second three-dimensional network of fibers 40 may be a three-dimensional network of mycelium fibers. Furthermore, the second layer of the filtration material 30 may be adhered to the first layer of filtration material 26 by the α-glucan of the first plurality of cells 38 or the second plurality of cells 42.

As further depicted in FIGS. 4 and 5, the first layer of filtration material 26 may have a first porosity 44, while the second layer of filtration material 30 may have a second porosity 46. For example, the second layer of filtration material 30 may have a smaller porosity than the first layer of filtration material 26. Accordingly, the second layer of filtration material 30 may be configured to preclude passage of solid materials of a filtrate stream 48 of the first layer of filtration material 26 as depicted in FIG. 3. As further seen in FIG. 3, the first layer of filtration material 26 may define a first plane 50, while the second layer of filtration material 30 may define a second plane 52. Further, an axis of rotation 54 that coincides with the contaminated air stream 16, the filtrate stream 48 and purified air stream 20, may extend through the first plane 50 and second plane 52. Further, the second plane 52 may be rotated by about forty five degrees with respect to the first plane 50 about the axis of rotation 54. Accordingly, in this instance, the second layer of filtration material 30 may be configured to preclude passage of solid materials of the filtrate stream 48 of the first layer of filtration material 26.

Additionally, as described before, the contaminated airstream 16 may include a gaseous contaminant such as a herbicide or pesticide vapor. Accordingly, as depicted in FIG. 3, the first layer of filtration material 26 and the second layer of filtration material 30 may include an adsorbent material 56 configured to preferentially adsorb the gaseous contaminant. Example materials configured to adsorb gaseous contaminants such as herbicide and pesticide vapors include, but are not limited to, high surface area (greater than about 10 $m^2/g$, preferably greater than about 75 $m^2/g$) alumina, microporous zeolites (preferably with particle sizes less than about 1 mm), other microporous materials, mesoporous materials, ordered mesoporous materials, and the like, and combinations thereof. Non-limiting examples of these materials can include carbon, cationic zeolites, high silica zeolites, zeolite molecular sieves, highly siliceous ordered mesoporous materials, sol-gel materials, ALPO materials (microporous and/or mesoporous materials containing predominantly aluminum, phosphorous, and oxygen), SAPO materials (microporous and/or mesoporous materials containing predominantly silicon, aluminum, phosphorous, and oxygen), MOF materials (microporous and/or mesoporous materials comprised of a metal organic framework), ZIF materials (microporous and/or mesoporous materials comprised of zeolitic imidazolate frameworks), microporous and/or mesoporous sorbent functionalized with functional groups (e.g., including primary, secondary, and tertiary amines, other non-protogenic basic groups such as amidines, guanidines, biguanides, and the like, as well as combinations thereof), and combinations and intergrowths thereof.

Figure 7:
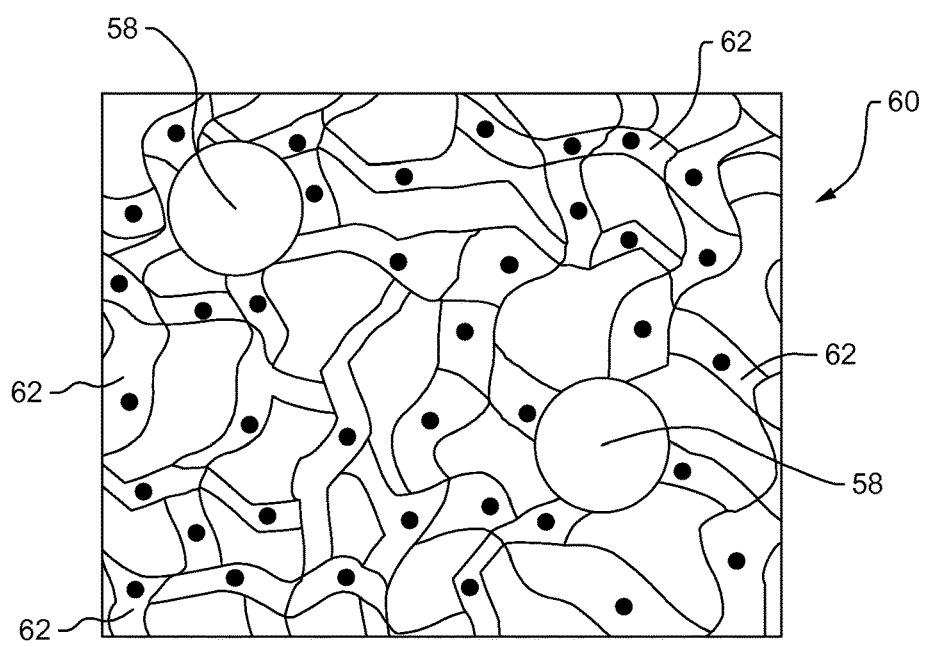
FIG. 7 is an enlarged plan view of portion 7 of FIG. 6.

Turning now to FIG. 6, an exemplary frame 34 that may be utilized with the filter assembly 18 of the present disclosure is illustrated. As depicted there, the frame 34 may include plurality of cellulosic fibers 58 having a length to diameter ratio of at least ten to one substantially aligned in the same direction. Exemplary examples of cellulosic fibers 58 that may be used with the frame 34 include, but are not limited to, jute, sisal, flax, hemp, coir, switchgrass and kenaf. Further, the frame 34 may comprise a third three-dimensional network of fibers 60. Turning now to FIG. 7, the third three-dimensional network of fibers 60 may include a third plurality of cells 62, and the third plurality of cells 62 may include an extracellular matrix including α-glucan and chitin. The extracellular matrix of the third plurality of cells 62 may include α-glucan and chitin because the third three-dimensional network of fibers 60 may be a third three-dimensional network of mycelium fibers. Returning to FIG. 6, the third three-dimensional network of fibers 60 may envelop the plurality of cellulosic fibers 58.

Turning now to FIGS. 8, 9 and 10 enlarged plan views depicting additional features of the three-dimensional network of fibers 36, 40, 60 of present disclosure are depicted. More specifically, as shown there, the first three-dimensional network of fibers 36, the second three dimensional network of fibers 40 and the third three-dimensional network of fibers 60 may be coated with a polymer mixture 64. The polymer mixture 64 may include a polymer 66 configured to mitigate exposure of the first three-dimensional network of fibers 36, the second three dimensional network of fibers 40 and the third three-dimensional network of fibers 60 to glucanases and chitanases, such as glucanases and chitanases that may be found in the contaminated air stream 16 when the filter assembly 18 is used in the air supply system 10. On the other hand, the polymer 66 may be configured to begin thermally degrading at or above a predetermined temperature, such as the temperature of a landfill or compost pile in which the filter assembly 18 may be disposed, thereby exposing the extracellular matrices to glucanases and chitanases leading to dergradation of the filter assembly 18. Exemplary examples of polymers 66 configured to mitigate exposure of the configured to mitigate exposure of the first three-dimensional network of fibers 36, the second three dimensional network of fibers 40 and the third three-dimensional network of fibers 60 to glucanases and chitanases, and begin thermally degrading at or above a predetermined temperature include, but are not limited to, polyvinyl benzene, ethylene vinyl acetate, polyethylene, polypropylene, polystyrene, polyethylene terephthalate, polyvinyl chloride, polylactic acid and mixtures thereof.

The polymer mixture 64 may further include an antioxidant 68 included in an amount sufficient to mitigate the polymer 66 from thermally degrading below the predetermined temperature, while allowing thermal degradation of the polymer 66 at or above the predetermined temperature, such as the temperature of a landfill or compost pile in which the filter assembly 18 may be disposed. While the following list is only exemplary, antioxidants 68 that may be added to the polymer mixture 64 include dicarboxylic acids such as oxalic acid, malonic acid, succinic acid, glutaric acid, adipic acid, pimelic acid, suberic acid, azealaic acid, sebacic acid, and the like, α-tocopherol, thioesters and mixtures thereof.

INDUSTRIAL APPLICABILITY

In operation, the teachings of the present disclosure can find applicability in many industrial applications, such as, but not limited to, an air supply system 10 for providing providing a purified air stream 20 to a vehicle cabin 24. The vehicle cabin 24 may be associated with, for example, an automobile, an on-highway truck, an earth moving machine, a track-type tractor, a combine, a tractor, or the like. In a preferred embodiment, the air supply system 10 may be used to provide air to an off-highway truck, such as those used in the mining and quarry industries. However, the air supply system 10 may be associated with any industry including, but not limited to, transportation, construction, forestry, agriculture, material handling and the like. Further, the present disclosure may alternatively find use with providing a purified air stream 20 to an internal combustion engine such as a reciprocating piston engine or a gas turbine engine, for example. Further, the teachings of the present disclosure may be utilized in heating, ventilation and air condition systems.

Referring now to FIG. 11, an exemplary flowchart is shown depicting a sample sequence of steps that may be followed to manufacture a filter assembly 18 according to the present disclosure. Step 70 of the method may include growing mycelium for a period of one to twenty days while exposed to a magnetic field to produce a live first layer of filtration material 26 comprising a first three-dimensional network of fibers 36 and curing the live first layer of filtration material 26 comprising a first three-dimensional network of fibers 36 by at a temperature of at least one hundred and fifty degrees Fahrenheit to terminate growth of the live first layer of filtration material 26 comprising a first three-dimensional network of fibers 36.

At a step 72, the method may include growing mycelium for a period of one to twenty days while exposed to a magnetic field to produce a live second layer of filtration material 30 comprising a second three-dimensional network of fibers 40 and curing the live second layer of filtration material 30 comprising a second three-dimensional network of fibers 40 at a temperature of at least one hundred and fifty degrees Fahrenheit to terminate growth of the live second layer of filtration material 30 comprising a second three-dimensional network of fibers 40.

Additionally, at a step 74, the method may include arranging a plurality of cellulosic fibers 58 in one direction and growing mycelium for a period of one to twenty days while exposed to a magnetic field to produce a frame 34 including a live third three-dimensional network of fibers 60, the live third three-dimensional network of fibers 60 enveloping the plurality of cellulosic fibers 58 and curing the live third three-dimensional network of fibers 60 at a temperature of at least one hundred and fifty degrees Fahrenheit to terminate growth of the live third three-dimensional network of fibers 60.

Additionally, the method of manufacturing the filter assembly 18 may further include layering the cured second layer of filtration material 30 comprising a second three-dimensional network of fibers 40 onto the cured first layer of filtration material 26 comprising a first three-dimensional network of fibers 36 and exposing the second layer of filtration material 30 and the first layer of filtration material 26 to a vacuum and pressure to adhere the second layer of filtration material 30 to the first layer of filtration material 26. The method may further include coating the first three-dimensional network of fibers 36, the second three-dimensional network of fibers 40 and the third three-dimensional network of fibers 60 with a polymer mixture 64, the polymer mixture 64 may include a polymer 66 and an antioxidant 68, the polymer 66 configured to mitigate exposure of the first three-dimensional network of fibers 36, the second three-dimensional network of fibers 40 and the third three-dimensional network of fibers 60 to glucanases and chitaneses, the polymer 66 further configured to begin thermally degrading at or above a predetermined temperature, the antioxidant 68 being included at an amount sufficient to mitigate the polymer 66 from thermally degrading below the predetermined temperature.

The above description is meant to be representative only, and thus modifications may be made to the embodiments described herein without departing from the scope of the disclosure. Thus, these modifications fall within the scope of present disclosure and are intended to fall within the appended claims.

What is claimed is:

1. A filtration material for filtering a contaminated air stream, comprising:
    a first layer comprising a first three-dimensional network of mycelium fibers including a first plurality of cells, the first plurality of cells including an extracellular matrix comprising α-glucan and chitin, the first layer configured to preclude passage of solid materials of the contaminated air stream;
    a second layer fluidly downstream of the first layer comprising a second three-dimensional network of mycelium fibers including a second plurality of cells, the second plurality of cells including an extracellular matrix including α-glucan and chitin, the second layer configured to preclude passage of solid materials of the contaminated air stream, the second layer being adhered to the first layer; and
    a polymer mixture coating the first layer and the second layer, the polymer mixture including a polymer and an antioxidant, the polymer configured to mitigate exposure of the first three-dimensional network of mycelium fibers and the second three-dimensional network of mycelium fibers to glucanases and chitaneses, the polymer further configured to begin thermally degrading at or above a predetermined temperature, the antioxidant being included at an amount sufficient to mitigate the polymer from thermally degrading below the predetermined temperature.

2. The filtration material according to claim 1, the second layer being adhered to the first layer by the α-glucan of the first plurality of cells or the second plurality of cells.

3. The filtration material according to claim 1, wherein the first plurality of cells including an extracellular matrix comprising α-glucan and chitin includes a first plurality of mycelium cells, the first plurality of mycelium cells including an extracellular matrix comprising α-glucan and chitin.

4. The filtration material according to claim 3, wherein the second plurality of cells including an extracellular matrix comprising α-glucan and chitin includes a second plurality of mycelium cells, the second plurality of mycelium cells including an extracellular matrix comprising α-glucan and chitin.

5. The filtration material according to claim 1, the first layer having a first porosity and the second layer having a second porosity, and wherein the second layer is further configured to preclude passage of solid materials of a filtrate stream of the first layer.

6. The filtration material according to claim 1, the first layer defining a first plane, the second layer defining a second plane, further including an axis of rotation extending through the first plane and the second plane, the second plane being rotated by about forty five degrees with respect to the first plane about the axis of rotation, and wherein the second layer is further configured to preclude passage of solid materials of a filtrate stream of the first layer.

7. The filtration material according to claim 1, the contaminated air stream including a gaseous contaminant, the first layer further including an adsorbent material configured to preferentially adsorb the gaseous contaminant.

8. The filtration material according to claim 7, the second layer further including the adsorbent material configured to preferentially adsorb the gaseous contaminant, and wherein the second layer is configured to preferentially adsorb the gaseous contaminant from a filtrate stream of the first layer.

9. A filter assembly for filtering a contaminated air stream, comprising:
    a first layer of filtration material comprising a first perimeter and first three-dimensional network of mycelium fibers including a first plurality of cells, the first plurality of cells including an extracellular matrix comprising α-glucan and chitin, the first layer of filtration material configured to preclude passage of solid materials of the contaminated air stream;
    a second layer of filtration material fluidly downstream of the first layer comprising a second perimeter and a second three-dimensional network of mycelium fibers including a second plurality of cells, the second plurality of cells including an extracellular matrix including α-glucan and chitin, the second layer of filtration material configured to preclude passage of solid materials of the contaminated air stream, the second layer of filtration material being adhered to the first layer of filtration material;
    a frame surrounding the first perimeter and the second perimeter including a plurality of cellulosic fibers having a length to diameter ratio of at least ten to one, the frame further including a third three-dimensional network of fibers including a third plurality of cells, the third plurality of cells including an extracellular matrix comprising α-glucan and chitin, the third plurality of cells enveloping the plurality of cellulosic fibers, the frame being configured to retain the first layer of filtration material and the second layer of filtration material; and
    a polymer mixture coating the first three-dimensional network of mycelium fibers, the second three-dimensional network of mycelium fibers and the third three-dimensional network of fibers, the polymer mixture including a polymer and an antioxidant, the polymer configured to mitigate exposure of the first three-dimensional network of mycelium fibers, the second three-dimensional network of mycelium fibers and the third three-dimensional network of fibers to glucanases and chitaneses, the polymer further configured to begin thermally degrading at or above a predetermined temperature, the antioxidant being included at an amount sufficient to mitigate the polymer from thermally degrading below the predetermined temperature.

10. The filter assembly according to claim 9, the second layer of filtration material being adhered to the first layer of filtration material by the α-glucan of the first plurality of cells or the second plurality of cells.

11. The filter assembly according to claim 9, wherein the first plurality of cells including an extracellular matrix comprising α-glucan and chitin includes a first plurality of mycelium cells, the first plurality of mycelium cells including an extracellular matrix comprising α-glucan and chitin.

12. The filter assembly according to claim 9, wherein the second plurality of cells including an extracellular matrix comprising α-glucan and chitin includes a second plurality of mycelium cells, the second plurality of mycelium cells including an extracellular matrix comprising α-glucan and chitin.

13. The filter assembly according to claim 9, the third three-dimensional network of fibers including a third plurality of cells, the third plurality of cells including an extracellular matrix comprising α-glucan and chitin being a third three-dimensional network of mycelium fibers including a third plurality of mycelium cells, the third plurality of mycelium cells including an extracellular matrix comprising α-glucan and chitin.

14. The filter assembly according to claim 9, the first layer of filtration material having a first porosity and the second layer of filtration material having a second porosity, and wherein the second layer is further configured to preclude passage of solid materials of a filtrate stream of the first layer of filtration material.

15. The filter assembly according to claim 9, the first layer of filtration material defining a first plane, the second layer of filtration material defining a second plane, further including an axis of rotation extending through the first plane and the second plane, the second plane being rotated by about forty five degrees with respect to the first plane about the axis of rotation, and wherein the second layer of filtration material is further configured to preclude passage of solid materials of a filtrate stream of the first layer of filtration material.

16. The filter assembly according to claim 9, the contaminated air stream including a gaseous contaminant, the first layer of filtration material further including an adsorbent material configured to preferentially adsorb the gaseous contaminant.

17. The filter assembly according to claim 16, the second layer further including the adsorbent material configured to preferentially adsorb the gaseous contaminant, and wherein the second layer is configured to preferentially adsorb the gaseous contaminant from a filtrate stream of the first layer.

18. The filter assembly according to claim 9, the frame being configured to retain the first layer of filtration material and the second layer of filtration material by compression fit.

* * * * *